US007807643B2

(12) United States Patent
Kirwin et al.

(10) Patent No.: US 7,807,643 B2
(45) Date of Patent: *Oct. 5, 2010

(54) COMPOSITIONS CONTAINING LEPTIN

(75) Inventors: Susan M. Kirwin, Thornton, PA (US); Vicky L. Funanage, Wilmington, DE (US)

(73) Assignee: The Nemours Foundation, Wilmington, DE (US)

( * ) Notice: Subject to any disclaimer, the term of this patent is extended or adjusted under 35 U.S.C. 154(b) by 75 days.

This patent is subject to a terminal disclaimer.

(21) Appl. No.: 12/034,419

(22) Filed: Feb. 20, 2008

(65) Prior Publication Data

US 2008/0242612 A1    Oct. 2, 2008

Related U.S. Application Data

(60) Division of application No. 10/286,947, filed on Nov. 4, 2002, now Pat. No. 7,354,896, which is a continuation of application No. 09/302,117, filed on Apr. 29, 1999, now Pat. No. 6,475,984.

(51) Int. Cl.
*A61K 38/19* (2006.01)
*G01N 33/24* (2006.01)
(52) U.S. Cl. .............................. 514/12; 530/351; 436/23
(58) Field of Classification Search .................. None
See application file for complete search history.

(56) References Cited

U.S. PATENT DOCUMENTS

| 4,994,496 A | 2/1991 | Repasky et al. ............. 514/775 |
| 5,298,246 A | 3/1994 | Yano et al. .................. 424/94.1 |
| 5,552,522 A | 9/1996 | DiMarachi et al. .......... 530/324 |
| 5,552,523 A | 9/1996 | Basinski et al. ............. 530/324 |
| 5,552,524 A | 9/1996 | Basinski et al. ............. 530/323 |
| 5,756,461 A | 5/1998 | Stephens ..................... 514/12 |
| 5,773,416 A | 6/1998 | Chehab ....................... 514/21 |
| 5,789,198 A | 8/1998 | Akerblom ................... 435/69.1 |
| 5,795,909 A | 8/1998 | Shashoua et al. ............ 514/449 |
| 5,830,450 A | 11/1998 | Lallone ...................... 424/85.1 |
| 5,866,547 A | 2/1999 | Flier et al. .................... 514/21 |
| 5,874,535 A | 2/1999 | Bailleul et al. .............. 530/350 |
| 5,882,860 A | 3/1999 | Snodgrass et al. .............. 435/6 |
| 5,942,540 A | 8/1999 | Kozachuk ................... 514/483 |
| 6,022,737 A | 2/2000 | Niven et al. ................ 435/320.1 |

OTHER PUBLICATIONS

Smith-Kirwin, Leptin expression in human mammary epithelial cells and breast milk, 1998, The Journal of Clinical Endocrinology and Metabolism, vol. 83, Issue 5, pp. 1810-1813.*
"Serum leptin concentrations in infants: effects fo diet, sex, and adiposity" by Bo Lonnerdal and Peter J. Havel; American Journel Clinical Nutrition 2000: 72: pp. 484-489.
Crawford et al, "Essential Fatty Acid Requirements in Infancy", *The American Journal of Clinical Nutrition*, vol. 31, pp. 2181-2185, Dec. 1978.

Dukas et al, "Quantitation of Changes in the Expression of Multiple Genes by Simultaneous Polymerase Chain Reaction", *Analytical Biochemistry*, vol. 215, pp. 66-72, 1993.
Gomm et al, "Separated Human Breast Epithelial and Myoepithelial Cells Have Different Growth Factor Requirements In Vitro But Can Reconstitute Normal Breast Lobuloalveolar Structure", *Journal of Cellular Physiology*, vol. 117, pp. 11-19, 1997.
Halaas et al, "Physilogical Response to Long-term Peripheral and Central Leptin Infusion in Lean and Obese Mice", *Proc. Natl. Acad. Sci. USA*, vol. 94, pp. 8878-8883, Aug. 1997.
Murphy et al, "Long-Term Correction of Obesity and Diabetes in Genetically Obese Mice by a Single Intramuscular Injection of Recombinant Adeno-Associated Virus Encoding Mouse Leptin", *Proc. Natl. Acad. Sci. USA*, vol. 94, pp. 13921-13926, Dec. 1997.
Hamosh et al, "Lipids in Milk and the First Steps in Their Digestion", *Pediatrics*, vol. 75 (suppl.), 1984, pp. 146-150.
Guisez et al, "Efficient Secretion of Biologically Active Recombinant OB Protein (Leptin) In *Escherichia coli*, Purification from the Periplasm and Characterization", *Protein Expression and Purification*, vol. 12, pp. 249-258 ,1998.
Loffreda et al, "Leptin Regulates Proinflammatory Immune Responses", *The FASEB Journal*, vol. 12, pp. 57-65, 1998.
Strobel et al, "A Leptin Missense Mutation Associated with Hypogonadism and Morbid Obesity", *Nature Genetics*, vol. 18, pp. 213-215, 1998.
Giuffrida et al, "Isolation and Characterization of Full and Truncated Forms of Human Breast Carcinoma Protein BA46 from Human Milk Fat Globule Membranes", *Journal of Protein Chemistry*, vol. 17, No. 2, pp. 143-148, 1998.
Hill et al, "Leptin: Its Pharmacokinetics and Tissue Distribution", *International Journal of Obesity*, vol. 22, pp. 765-770, 1998.
Tartaglia et al, "Identification and Expression Cloning of a Leptin Receptor, OB-R", *Cell*, vol. 83, pp. 1263-1271, 1995.
Cioffi et al, "Novel B219/OB Receptor Isoforms: Possible Role of Leptin in Hematopoiesis and Reproduction", *Nature Medicine*, vol. 2, No. 5, pp. 585-589, 1996.
Clement et al, "A Mutation in the Human Leptin Receptor Gene Causes Obesity and Pituitary Dysfunction", *Nature*, vol. 392, pp. 398-401, 1998.
Friedman et al, "Leptin and the Regulation of Body Weight in Mammals", *Nature*, vol. 395. pp. 763-770, 1998.
Houseknecht et al, "Evidence for Leptin Binding to Proteins in Serum of Rodents and Humans: Modulation with Obesity", *Diabetes*, vol. 45, pp. 1638-1643, 1996.

(Continued)

*Primary Examiner*—Robert Landsman
*Assistant Examiner*—Ian Dang
(74) *Attorney, Agent, or Firm*—Townsend and Townsend and Crew LLP

(57) ABSTRACT

A method and composition for administering leptin to a subject. The invention includes suspending isolated native leptin-containing milk fat globules in a suitable medium for administering to a subject. The suspended milk fat globules may be administered orally as well as by intravenous, intramuscular, intraperitone41, other enteral routes of administration, and other parenteral routes of administration. The invention includes a method for treating growth or maturational-related disorders in newborns as, well as subjects having conditions that can be treated by the administration of leptin.

23 Claims, 5 Drawing Sheets

OTHER PUBLICATIONS

Murphy et al, "Long-term Correction of Obesity and Diabetes in Genetically Obese Mice by a Single Intramuscular Injection of Recombinant Adeno-Associated Virus Encoding Mouse Leptin", *Proc. Natl. Acad. Sci. USA*, vol. 94, pp. 13921-13926, 1997.

Halaas et al, "Physiological Response to Long-term Peripheral and Central Leptin Infusion in Lean and Obese Mice", *Proc. Natl. Acad. Sci. USA*, vol. 94, pp. 8878-8883, 1997.

Senaris et al, "Synthesis of Leptin in Human Placenta", *Rapid Communications*, vol. 138, No. 10, pp. 4501-4504, 1997.

Considine et al, "Serum Immunoreactive-Leptin Concentrations in Normal-weight and Obese Humans", *The New England Journal of Medicine*, pp. 292-325, 1996.

Marquez-ruiz et al, "Modification of Triacylglycerides and Apolipoprotein in Rats Fed Diets Containing Whole Milk, Skim Milk and Milk Proteins", *American Institute of Nutrition*, pp. 1840-1846, 1992.

Levin et al, "Cell-Cell Interactions Promote Mammary Epithelial Cell Differentiation", *The Journal of Cell Biology*, vol. 100, pp. 1415-1422, 1985.

Wiens et al, "Milk Protein Expression and Ductal Morphogenesis in the Mammary Gland in Vitro: Hormone-Dependent and Independent Phases of Adipocyte-Mammary Epithelial Cell Interaction", *Developmental Biology*, vol. 120, pp. 245-258, 1987.

Rayner et al, "Postnatal Development of the *ob* Gene System: Elevated Leptin Levels in SuckIng fa/fa Rats", *Rapid Communication*, pp. R446-R450, 1997.

Casabiell et al, "Presence of Leptin in Colostrum and/or Breast Milk from Lactating Mothers: A Potential Role in the Regulation of Neonatal Food Intake", *Journal of Clinical Endocrinology and Metabolism*, vol. 82, No. 1, pp. 4270-4272, 1997.

Gainsford et al, "Leptin can Induce Proliferation, Differentaition, and Functional Activation of Hemopoietic Cells" *Proct. Natl. Acad. Sci. USA*, vol. 93, pp. 14564-14568, 1996.

Lord et al, "Leptin Modulates the T-cell Immune Response and Reverses Starvation-induced Immunosuppression", *Nature*, vol. 394, pp. 897-901, 1998.

Lepercq et al, "Overexpression of Placental Leptin in Diabetic Pregnancy", *Diabetes*, vol. 47, pp. 847-850, 1998.

Houseknecht et al, "Leptin is Present in Human Milk and is Related to Maternal Plasma Leptin Concentration and Adiposity", *Biochemical and Biophysical Research Communications*, vol. 240, No. 3, pp. 742-747, 1997.

Flier, "Lowered Leptin Slims Immune Response", *Nature Medicine*, vol. 4, No. 10, pp. 1124-1125, 1998.

Georgieff et al, "Mid-arm Curcumference/Head Circumference Ratios for Identification of Symptomatic LGA, AGA, and SGA Newborn Infants", *The Journal of Pediatrics*, vol. 109, No. 2, pp. 316-321, 1986.

Patton et al, "A Method for Isolation of Milk Fat Globules", *Lipids*, vol. 21, No. 2, pp. 170-175, 1986.

Trottier et al, "Increased Fat Intake During Lactation Modifies Hypothalamic-Pituitary-Adrenal Responsiveness in Developing Rat Pups: A Possible Role for Leptin", *Endocrinology*, vol. 139, No. 9, pp. 3704-3711, 1998.

Chehab et al, "Early Onset of Reproductive Function in Normal Female Mice Treated with Leptin", *Science*, vol. 275, pp. 88-90, 1997.

Zhang et al, "Positional Cloning of the Mouse Obese Gene and Its Human Homologue", *Nature*, vol. 372, pp. 425-431, 1994.

Shimabukuro at al, "Direct Antidiabetic Effect of Leptin Through Triglyceride Depletion of Tissues", *Proc. Natl. Acad. Sci. USA*, vol. 94, pp. 4637-4641, 1997.

Brooker et al, "The Epithelial Cells and Cell Fragments in Human Milk" *Cell Tissue Res.*, vol. 210, pp. 321-332, 1980.

Spear et al, "Leptin Predicts Somacle Growth in Premature Infant", *Neonatal Nutrition & Metabolism*, Abstract, No. 1713, 1999.

Steppan et al, "A Role for Leptin in Brain Development", *Biochem. Biophy. Res. Comm.*, vol. 256, 1999, pp. 600-602.

Schubring et al, "Rapid Decline of Serum Leptin Levels in Healthy Neonates After Birth", *Eur. J. Pediatr.*, vol. 157(3), pp. 263-264.

Hartmann et al, "Maternal and Umbilical-cord Serum Leptin Concentrations in Normal, Full-term Pregnancies", *N. Engl. J. Med.*, vol. 337(12), p. 863, 1997.

Chen et al, "Disappearance of Body Fat in Normal Rats Included by Adenovirus-medicated Leptin Gene Therapy", *Proc. Natl. Acad. Sci.*, vol. 93, pp. 14795-14799, 1996.

Kamohara et al, Acute Stimulation of Glucose Metabolism in Mice by Leptin Treatment, *Nature*, vol. 389(6649), pp. 374-377, 1997.

Zittle et al, The Fat-globule Membrane of Milk: Alkaline Phosphate and Xanthine Oxidase in Skimmilk and Cream, *J. Dairy Sci.*, vol. 39, pp. 528-535, 1956.

Tankersley et al., "Leptin Attenuates Respiratory Complications Associated with the Obese Phenotype", J Appl Physiol, Dec. 1998, pp. 2261-2269.

Sierra-Honigmann et al., "Biological Action of Leptin as an Angiogenic Factor", Science, vol. 281, Sep. 11, 1998, pp. 1683-1686.

Bado et al., "The Stomach is a Source of Leptin", Letters to Nature, vol. 394, Aug. 20, 1998, pp. 790-793.

Koronen et al., "Is Brain Uptake of Leptin In Vivo Saturable and Reduced by Fasting?", Eur J Nucl Med, vol. 25, Jun. 1998.

Yura et al., "A Positive Umbilical Venous-Arterial Difference of Leptin Level and Its Rapid Decline After Birth", Am J Obstet Gynecol, May 1998, pp. 926-930.

Marchini et al., "Plasma Leptin in Infants: Relations to Birth Weight and Weight Loss", Pediatrics, vol. 101, Mar. 1998, pp. 429-432.

Helland et al., "Leptin Levels in Pregnant Women and Newborn Infants: Gender Differences and Reduction During the Neonatal Period", Pediatrics, vol. 101, Mar. 1998, p. E12.

Tamura et al., "Serum Leptin Concentrations During Pregnancy and Their Relationship to Fetal Growth", Obstetrics & Gynecology, vol. 91, Mar. 1998, pp. 389-395.

Cawthorne et al., "Peripheral Metabolic Actions of Leptin", Proceedings of the Nutrition Society, 1998, pp. 449-453.

Bouloumie et al., "Leptin, the Product of Ob Gene, Promotes Angiogenesis", Circ Res, Nov. 14, 1998, pp. 1059-1066.

Shekhawat et al., "Neonatal Cord Blood Leptin: Its Relationship to Birth Weight, Body Mass Index, Maternal Diabetes and Steroids", Pediatric Research, Mar. 1998, pp. 338-343.

Jaquet et al., "Ontogeny of Leptin in Human Fetuses and Newborns", Journal of Endocrinology and Metabolism, 1998, pp. 1243-1246.

Stein et al., "Plasma Leptin Influences Gestational Weight Gain and Postpartum Weight Retention", Am J Clin Nutr, 1998, pp. 1236-1240.

Smith-Kirwin et al., "Leptin Expression in Human Mammary Epithelial Cells and Breast Milk", Journal of Clinical Endocrinology and Metabolism, May 1998, pp. 1810-1813.

Gavrilova et al., "Hyperleptinemia of Pregnancy Associated with the Appearance of a Circulating Form of the Leptin Receptor", The Journal of Biological Chemistry, Nov. 28, 1997, pp. 30546-30551.

Chehab, "The Reproductive Side of Leptin", Nature Medicine, vol. 3, Sep. 1997, pp. 952-953.

Masuzaki et al., "Nonadipose tissue Production of Leptin: Leptin As a Novel Placenta-Derived Hormone in Humans", Nature Medicine, vol. 3, Sep. 1997, pp. 1029-1033.

Sivan et al., "Leptin Is Present in Human Cord Blood", Diabetes, vol. 46, May 1997, pp. 917-919.

Harigaya et al., "Relationship Between Concentration of Serum Leptin and Fetal Growth", Journal of Clinical Endocrinology and Metaabolism, Oct. 1997, pp. 3281-3284.

Matsuda et al, "Serum Leptin Concentration in Cord Blood: Relationship to Birth Weight and Gender", Journal of Clinical Endocrinology and Metabolism, May 1997, pp. 1642-1644.

Schubring et al., "Levels of Leptin in Maternal Serum. Amniotic Fluid, and Arterial and Venous Cord Blook: Relation to Neonatal and Placental Weight", Journal of Clinical Endocrinology and Metabolism, 1997, pp. 1480-1483.

Butte, et al., "Leptin in Human Reproduction: Serum Leptin Levels in Pregnant And Lactating Women", Journal of Clinical Endocrinology and Metabolism, 1997, pp. 585-589.

Koistinen et al., "Leptin Concentration in Cord Blood Correlates With Intrauterine Growth", Journal of Clinical Endocrinology and Metabolism, Oct. 1997, pp. 3328-3330.

Hassink et al., "Placental Leptin: An Important New Growth Factor in Intrauterine and Neonatal Development?", Pediatrics, vol. 100, Jul. 1997, pp. E1-E6.

Hamosh, et al, "Lipids in Milk and the First Steps in Their Digestion", Pediatrics vol. 75 (suppl.), 1984, pp. 146-150.

Giuffrida et al "Isolation and Characterization of Full and Truncated Forms of Human Breast Carcinoma Protein BA46 from Human Milk Fat Globule Membranes", Journal of Protein Chemistry, vol. 17. No. 2, pp. 143-148, 1998.

Clement et al "A Mutation into Human Leptin Receptor Gene Causes Obesity and Pituitary Dysfunction", Nature, vol. 392, pp. 398-401, 1998.

Houselcnecht et al, "Evidence for Leptin Binding to Proteins in Serum of Rodents and Humans: Modulation with Obesity", Diabetes, vol. 45, pp. 1638-1643, 1996.

Senaris et al, "Synthesis of Leptin in Human Placenta", Rapid Communications, vol. 138, No. 10, pp. 4501-4504, 1997.

Dukas et al, "Quantitation of Changes in the Expression of Multiple Genes by Simultaneous Polymerase Chain Reaction", Analytical Biochemistry, vol. 215, pp. 66-72, 1993.

Leporeq et al, "Overexpression of Placental Leptin in Diabetic Pregnancy", Diabetes, vol. 47, pp. 847-850, 1998.

Georgieff et al, "Mid-arm Curcumference/Head Circumference Ratios for Identification of Symptomatic LGA, AGA, nad SGA Newborn Infants", The Journal of Pediatrics, vol. 109, No. 2, pp. 316-321, 1986.

Shimabukuro et al, "Direct Antidiabetic Effect of Leptin Through Triglyceride Depletion of Tissues", Proc. Natl. Acad. Sci. USA, vol. 94, pp. 4637-4641, 1997.

Brooker et al, "The Epithelial of Cells and Cell Fragments in Human Milk", Cell Tissue Res., vol. 210, pp. 321-332, 1980.

Schubring et al, "Rapid Decline of Serum Leptin Levels in Healthy Nonates After Birth", Eur. J. Pediatr., vol. 157(3), pp. 263-264.

Kamohara et al, "Acute Stimulation of Glucose Metabolism in Mice by Leptin Treatment", Nature, vol. 389(6649), pp. 374-377, 1997.

Zittle et al, "The Fat-globule Membrane of Milk: Alkaline Phosphate and Xanthine Oxidase in Skimmilk and Cream", J. Dairy Sci., vol. 39, pp. 528-535, 1956.

Tankersley et al., "Leptin Attenuates Respiratory Complications Associated with the Obese Phenotype", J. Appl Physiol, Dec. 1998, pp. 2261-2269.

Cawthorne et al., "Peripheral Metabolic Actions of Leptin", Proceedings of the Nutrition Society, 1998, pp. 449-453.

Boulomie et al., "Leptin, the Product of Ob Gene, Promotes Angiogenesis", Circ Res, Nov. 14, 1998, pp. 1059-1066.

Shekhawat et al., "Neonatal Cord Blood Leptin" Its Relationship to Birth Weight, Body Mass Index, Maternal Diabetes and Steroids, Pediatric Research, Mar. 1998, pp. 338-343.

Matsuda et al., "Serum Leptin Concentration in Cord Blood: Relationship to Birth Weight and Gender", Journal of Clinical Endocrinology and Metabolism, May 1997, pp. 1642-1644.

Schubring et al., "Levels of Leptin In Maternal Serum, Amniotic Fluid, and Arterial and Venous Cord Blood: Relation to Neonatal and Placental Weight", Journal of Clinical Endocrinology and Metabolism, 1997, pp. 1480-1483.

Crawford et al., "Essential Fatty Acid Requirements in Infancy", The American Journal of Clinical Nutrition, vol. 31, pp. 2181-2185, Dec. 1978.

"Serum Leptin Concentrations in Infants: Effects of Diet, Sex, and Adiposity" by Bo Lonnerdal and Peter J. Havel; American Journal Clinical Nutrition 2000: 72: pp. 484-489.

* cited by examiner

RT/PCR Analysis of Leptin mRNA in Mammary Gland and Adipose Tissue

Immunohistochemical Detection of Leptin in Human Breast Tissue and Mammary Epithelial Cells

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 1
attctgcctc ttgctcagcc tgc                                    23

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 2
agctctctga gggtagggca ccac                                   24

COMPOSITIONS CONTAINING LEPTIN

CROSS-REFERENCES TO RELATED APPLICATIONS

This application is a divisional application of U.S. application Ser. No. 10/286,947, filed on Nov. 4, 2002, now U.S. Pat. No. 7,354,896, which in turn is a continuation of U.S. application Ser. No. 09/302,117, filed on Apr. 29, 1999, now U.S. Pat. No. 6,475,984, the disclosures of which are herein expressly incorporated by reference in their entirety.

BACKGROUND OF THE INVENTION

Leptin, the protein product of the ob gene, is an important circulating signal for regulating body weight, food intake, and energy metabolism in mammals (Zhang Y et al., *Nature*, 372: 425-432, 1994). These actions are elicited through the binding of leptin to a high affinity receptor in the hypothalamus (Tartaglia L A et al., *Cell*, 83: 1263-1271, 1995). Although leptin was initially described as a satiety factor that regulates the size of adipose tissue, leptin has many other diverse biological functions. These functions are elicited by the binding of leptin to receptor proteins that are expressed in numerous tissues.

Leptin has been shown to correct the sterility defect in leptin-deficient mice and accelerate puberty when administered to normal mice (Chehab et al. *Nature Genet.*, 12:318-320, 1996). Humans defective in either leptin or the leptin receptor are sterile and sexually immature, supporting leptin's role in reproduction (Stroebel et al., *Nature Genet.*, 18: 213-215, 1998; Clement et al., *Nature*, 392: 398-401, 1998). Other roles for leptin include a regulator of hematopoeisis (Cioffi et al., *Nature Medicine*, 2: 585-589, 1996; Gainsford et al., *Proc. Natl. Acad. Sci. USA*, 93: 14564-14568, 1996), angiogenesis (Bouloumie et al., *Circ. Res.*, 83: 1059-1066, 1998; Sierra-Honigmann et al., *Science*, 281: 1683-1686, 1998), glucose metabolism (Kamohara et al., *Nature*, 389: 374-377, 1997), and proinflammatory immune responses (Loffreda et al., *FASEB J*, 12:57-65, 1998; Lord et al., *Nature*, 394: 897-901, 1998). Since malnutrition is the leading cause of diminished immunity and increased susceptibility to infection, leptin therapy may also augment the immune response in compromised individuals (Flier, *Nature Medicine* 4: 1124-1125, 1998).

Although first thought to be produced exclusively by the adipocyte (fat cell), it is now known that leptin is produced in the placenta (Hassink et al., *Pediatrics*, 100:e1-e6, 1997; Masuzaki et al., Nature Med. 3: 1029-1033, 1997), gastric epithelium (Bado et al., *Nature*, 394:790-793, 1998), and the mammary gland, as more fully described below (Smith-Kirwin et al., *J. Clin. Endocrinol. Metab.*, 83: 1810-1813, 1998, herein incorporated by reference). The function of placental leptin seems to be as a regulator of fetal growth. Prematurity accounts for a large proportion of infant morbidity, primarily due to respiratory distress, immaturity of organ systems, and poor nutrition. As more fully described below, the premature infant is leptin-deficient, due to early separation from the placenta at a time when they have inadequate adipose tissue. A method to administer leptin to premature and/or poorly growing infants is highly desirable.

Previous leptin therapies rely on the use of recombinant leptin. The administration of recombinant leptin is performed intravenously, intramuscularly, intraperitoneal, and through other parenteral routes to treat obesity, diabetes, and reproductive abnormalities. The amount of leptin that can be delivered by these means is limited by recombinant leptin's poor solubility and by local reactions in skin that occur in response to high doses (Friedman and Halaas, *Nature*, 395: 763-770, 1998). In rodent models, it has been shown that the ability to optimize the means of administration of leptin may greatly influence its therapeutic effectiveness. Leptin has been shown to be more potent when administered as a subcutaneous infusion than when administered by daily intraperitoneal injections (Halaas et al., *Proc. Natl. Acad. Sci. USA*, 94: 8878-8883, 1997). Direct administration of leptin into the cerebrospinal fluid (Halaas et al., *Proc. Natl. Acad. Sci. USA*, 94: 8878-8883, 1997) and by gene therapy means (Chen et al., *Proc. Natl. Acad. Sci. USA*, 93: 14795-14799, 1996; Murphy et al., *Proc. Natl. Acad. Sci. USA*, 94: 13921-13926, 1997) have also been shown to be effective for weight loss in rodents, but for safety and ethical concerns have not been tried in humans.

Previous methods involving leptin therapies rely on the use of recombinant leptin. Purification of recombinant leptin involves denaturation of the protein and subsequent renaturation steps. The renatured leptin must then be solubilized, which is problematic because the recombinant leptin aggregates at high concentrations and much protein loss occurs (Guisez et al., *Protein Expression Purification*, 12: 249-258, 1998). The renatured leptin must then be tested for bioactivity.

Therefore, it is desirable to provide a method for administering leptin that does not require the use or purification of recombinant leptin that can be administered orally, intravenously, subcutaneously, intramuscularly, intraperitoneally or by other parenteral means. As stated above, a method to administer leptin to premature and/or poorly growing infants is highly desirable.

As more fully described below, the present invention overcomes the problems associated with previous forms of leptin therapy and includes a novel method and composition for administering native leptin that can be administered to subjects who have deficient leptin levels or require leptin therapy to treat a disorder.

BRIEF SUMMARY OF THE INVENTION

The present invention includes a method and composition of native leptin in milk fat globules. This composition may be administered orally, intravenously, intramuscularly, intraperitoneally, or by other enteral or other parenteral means. In one embodiment, the invention includes a method for treating growth-related problems in newborns.

The invention includes a composition for the administration of leptin comprising isolated milk fat globules wherein the milk fat globules contain a native form of leptin.

The invention further includes isolated milk fat globules that are derived from a milk-producing mammal that produces milk fat globules containing a native form of leptin. The mammal may be selected from the group consisting of humans, cows, rats, mice, and goats.

The invention includes a medium that is effective for suspending the milk fat globules and is safe to administer to humans. Preferably the medium is selected from the group consisting of physiologic saline, water, intravenous fluid, milk, human breast milk, baby formula, and any other medium that is safe for human or infant administration.

The invention includes suspending the isolated milk fat globules in the medium at a concentration between about 50 ng/ml leptin and about 100 ng/ml leptin. Preferably, the isolated milk fat globules are suspended at a concentration of about 75 ng/ml.

Further, the invention includes isolated milk fat globules where at least a portion of the leptin is contained within the milk fat globules.

The invention includes a method for administering leptin that includes administering to a subject an effective amount of isolated native leptin-containing milk fat globules where the isolated native leptin-containing milk fat globules have been suspended in a medium to produce suspended milk fat globules.

The invention includes subjects that have a condition selected from the group consisting of obesity, sterility, sexual immaturity, malnutrition, compromised immunity, psychiatric disorders, diabetes, and subjects with a condition that can be treated by the administration of lentin.

Still further, the invention includes a subject selected from a group consisting of a premature infant, a full-term infant having low leptin levels, a low birth weight infant, and an infant with a condition that can be treated with leptin.

The present invention further includes administering an effective amount of suspended milk fat globules by an administration method selected from the group consisting of oral administration, subcutaneous administration, intramuscular administration, intravenous administration, intraperitoneal administration, and other enteral or parenteral routes of administration.

Still further, the present invention includes a method for administering leptin to infants that includes administering to the infant an effective amount of isolated native leptin-containing milk fat globules wherein the isolated native leptin-containing milk fat globules are suspended in a medium to produce suspended milk fat globules.

The invention includes a medium that is effective for suspending the milk fat globules and is safe to administer to infants. Preferably, the medium is selected from the group consisting of physiologic saline, water, intravenous fluid, milk, human breast milk, baby formula, soy milk, and any other medium that is safe for infant administration.

The invention includes administering an effective amount of leptin to an infant. Preferably, the effective amount is about 0.5 ng to about 1.0 ng of leptin per gram of infant body weight per feeding.

DETAILED DESCRIPTION OF THE INVENTION

The present invention is based on studies that show leptin is produced by the mammary gland and packaged in milk fat globules (MFGs). The inclusion of leptin in MFGs is believed to confer protection of leptin by proteases and the acid environment of the stomach. It may also provide a means by which leptin is solubilized as leptin is believed to be bound to other proteins in the circulation which modulate its bioactivity and bioavailability (Houseknecht et al., *Diabetes*, 45: 1638-1643, 1996; Hill et al., *Int. J. Obesity*, 22: 765-770, 1998). Purified recombinant leptin is insoluble and must be denatured before solubilization. Both Guisez et al. (*Protein Expression Purification*, 12: 249-258, 1998) and Campbell et al. (*Biochem. Biophys. Res. Comm.*, 247: 654-658, 1998) provide evidence for the binding of leptin to fatty acids, in particular oleic acid, palmitic acid, and arachidonic acid. These fatty acids are the same fatty acids that comprise the core of the MFG.

Purified MFGs provide a solubilized, stable, and native leptin preparation. Evidence for leptin inside the globule is derived from several recent studies, which are described in Smith-Kirwin et al. (*J. Clin. Endocrinol. Meta.*, 83: 1810-1813, 1998) herein specifically incorporated by reference and described in Example 1 below. Briefly summarized, the following points support the conclusion that leptin is associated with MFGs. First, increased leptin levels are found in the cream portion of whole milk and in isolated milk fat globules. Second, MFGs are positive for leptin by immunohistochemical staining, as are breast tissue, cultured mammary epithelial cells, and secretory epithelial cells present in human milk. Finally, MFGs must be disrupted by either mechanical or enzymatic means to detect leptin by radio immunoassay. This suggests that the epitopes recognized by the leptin antibody are normally not accessible in the intact MFG.

Low levels of immunodetectable leptin are found in whole milk. However, when whole milk is homogenized by mechanical disruption, leptin levels increase 100-fold. These results indicate that leptin is bound to a substance in the milk fat. This substance is the MFG.

Figure 1:
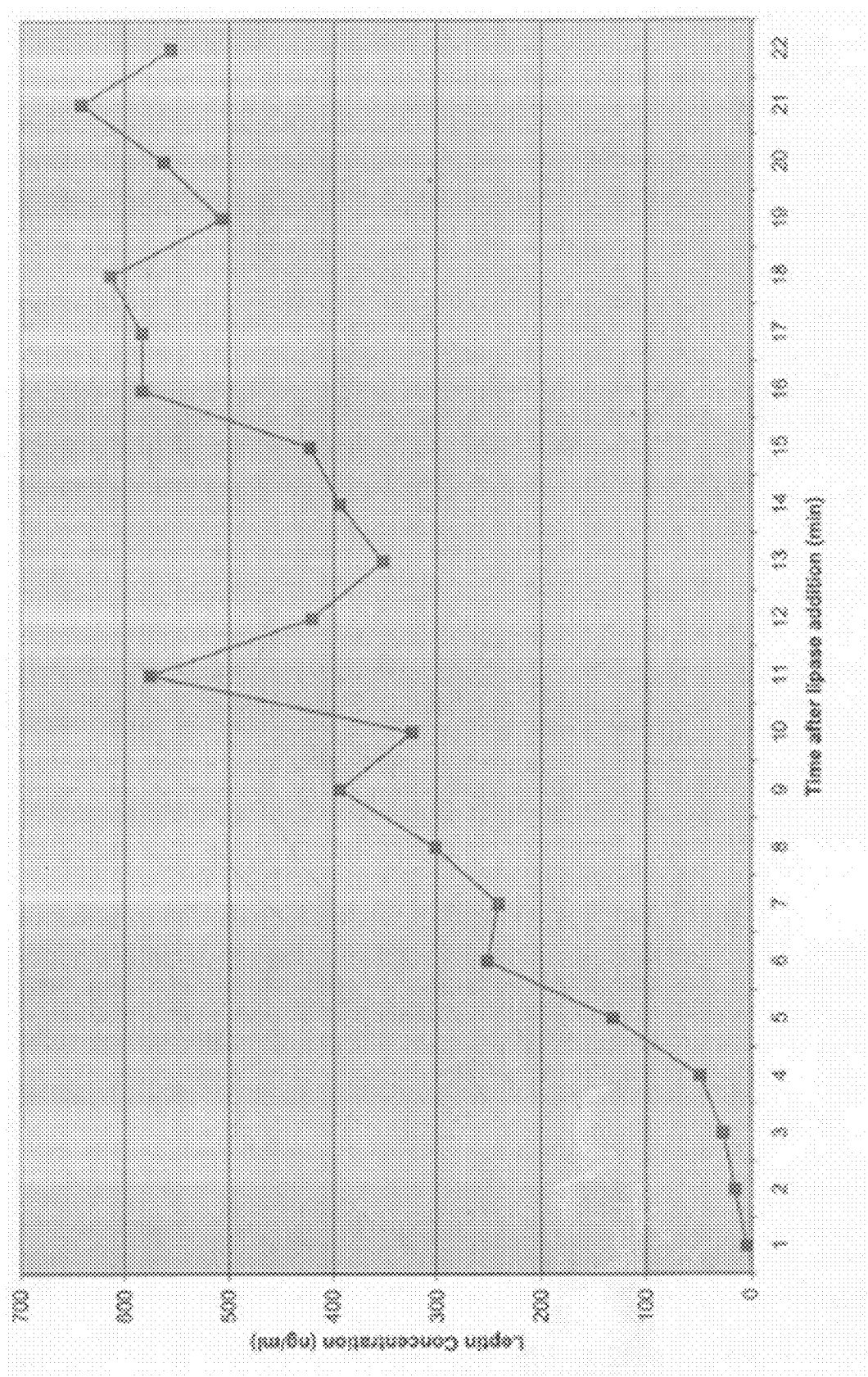
FIG. 1 is a plot of leptin concentration (ng/ml) as a function of time after the addition of pancreatic lipase.

With reference now to FIG. 1 and more fully explained in Example 2, isolated MFGs were treated with pancreatic lipase to determine the levels of leptin in the MFGs. FIG. 1 shows treatment of whole milk samples with 50 U/ml pancreatic lipase, which acts to breakdown triglyceride in the MFG, and measurement of released, immunodetectable leptin levels over time. Leptin release occurs in two phases, an initial rapid release which likely represents a loose association of leptin with the MFG, and a slower release, which indicates leptin is being released from a bound source, perhaps the fatty acids in the MFG.

A difficulty with the oral administration of leptin is that leptin is acid-labile and would not survive the acidic environment of the digestive system. The packaging of leptin in the MFG provides an oral means of administering leptin systematically. The MFG consists of a triglyceride core surrounded by a membrane that is pinched off from the apical membrane of breast epithelial cells and envelopes the milk fat.

MFGs can be isolated from any milk-producing mammal that produces leptin-containing MFGs in their milk. These mammals include but are not limited to humans, cows, rats, mice, and goats. As used herein "isolated MFGs" refers to native leptin-containing MFGs that have been isolated from any milk-producing mammal that produces native leptin-containing MFGs. Several methods to isolate MFGs have been described and are well known in the art such as the method described in Giuffrida et al., J. Prot. Chem. 17: 143-148, 1998 herein specifically incorporated by reference and Patton and Huston, Lipids 21: 170-174, 1986 herein specifically incorporated by reference. A preferred method is the technique described by Patton and Huston, in which MFGs were isolated from cow, goat, and human milk by centrifuging the MFGs through an overlaying buffer layer. It has been shown that 85% of the xanthine oxidase and alkaline phosphatase activities are removed from MFGs by four successive water washes (Zittle et al., *J. Dairy Sci.,* 39: 528-535, 1956 herein specifically incorporated by reference). Since a significant proportion of leptin is loosely bound to the MFG as described above, the method described by Patton and Huston would be expected to minimize the loss of leptin from MFGs.

The leptin concentration in MFGs may be determined by either sonication or lipase treatment of the MFGs followed by analysis of the treated milk sample by radioimmunoassay for immunodetectable leptin. Prior to administering the isolated MFGs to a subject, the isolated MFGs should be resuspended in a medium to produce suspended MFGs. As used herein, "suspended MFGs" means a solution in which the isolated MFGs have been reduced in concentration or diluted by the medium. The MFGs may be resuspended in a medium including, but not limited to, physiologic saline (0.9% wt/vol NaCl), water, intravenous solutions, human breast milk, milk, baby formula, or any other medium that is safe for human administration. The isolated MFGs are resuspended at a concentration between about 50 ng/ml leptin to about 100 ng/ml leptin and preferably resuspended at a concentration of 75 ng/ml.

The MFGs should be resuspended in a medium that is appropriate for the type of administration. If the MFGs are being administered orally, the MFGs should be resuspended in a medium appropriate for consumption. An appropriate medium includes, but is not limited to, human breast milk, milk, baby formula, soy milk, water, or other liquid safe for human consumption. If the MFGs are to be injected intravenously, subcutaneously, intraperitoneally, or intramuscularly, the MFGs should be suspended in an appropriate medium for injection including, but not limited to, physiologic saline, water, and other intravenous solutions. Additional supplements including, but not limited to, nutrients, drugs, or other substances may be added to the suspended MFGs prior to, during, or along with the administration of an effective amount of the suspended MFGs to a subject provided that the addition of the additional supplement does not prevent the effective administration of leptin to the subject.

An effective amount of suspended MFGs may be administered by any of the above referenced methods to subjects requiring leptin therapy to treat a disorder, also referred to herein as a "condition." These conditions include," but are not limited to, obesity, sterility, sexual immaturity, malnutrition, compromised immunity, psychiatric disorders, diabetes, and subjects with a disorder that would can be treated by the administration of leptin. Further, leptin may be administered to a subject to assist in the development of the brain.

Of particular importance is the applicability of the present invention to the treatment of infants. The function of placental leptin seems to be as a regulator of fetal growth. Leptin levels in cord blood are highly correlated with both the infant's birth weight and body mass index (Koistinen et al., *J. Clin. Endocrinol. Metab.,* 82: 3328-3330, 1997; Harigaya et al., *J. Clin. Endocrinol. Metab.,* 82: 3281-3284, 1997; Schubring et al., *J. Clin. Endo. Metab.,* 82: 1480-1483, 1997; Matsuda et al., *J. Clin. Endo. Metab.,* 82: 1642-1644, 1997; Tamura et al., *Obstet. Gynecol.,* 91: 389-395, 1998; Marchini et al., *Pediatrics,* 101: 429-432, 1998). Both large-for-gestational age and infants of diabetic mothers have higher cord blood leptin concentrations than appropriate-for-gestational age infants (Lepercq et al., *Diabetes,* 47: 847-850, 1998). Premature infants have low leptin levels, which increase 3-fold in mothers who receive steroids antenatally (Shekhawat et al., *Pediatr. Res.,* 43: 3338-3343, 1998). Interestingly, within 48 hours of delivery, the concentration of leptin in large-for-gestational age and appropriate-for-gestational age babies decreases to the level in small-for-gestational age infants. These low leptin levels continue to 7 days of age. Helland et al. (*Pediatrics,* 101: e12, 1998) have shown that leptin levels also decrease from birth to 4 weeks of age, but moderately increase thereafter. Furthermore, at all time points examined, leptin levels are significantly higher in female infants as compared to males.

As mentioned earlier, prematurity accounts for a large proportion of infant morbidity, primarily due to respiratory distress, immaturity of organ systems, and poor nutrition. The premature infant is leptin-deficient, due to early separation from the placenta at a time when they have inadequate adipose tissue stores.

Leptin concentrations were measured at semi-weekly intervals from birth through discharge (range 1-77 days) in 11 premature infants requiring mechanical ventilation (gestational age=28±2 weeks, birth weigh=986±189 g, mean±S.D.). At the time of leptin sampling, anthropometric measurements were obtained, and calculations of mid/arm circumference/head circumference ratio, and upper arm fat were made. One hundred fifty six measurements of leptin concentrations were obtained in this patient population (mean±SD=1.24±0.63 ng/ml, range=0-3). Using a multiple linear regression model, the best variables in this sample population to predict leptin levels were determined. The values that best predicted leptin, in descending order of variance, were: mid arm/head circumference ratio, lower arm circumference, calf circumference, postnatal age, upper arm fat, mid thigh circumference, daily weight, birth weight, and abdominal girth (r value=0.71, r-squared=0.51, p<0.00001).

A multiple linear regression using the variables measured in the investigation and the ratio of mid arm/head circumference as the dependent variable to reflect adequacy of growth in the premature infant was performed (Spear et al., *Pediatr. Res.,* 45(4):291A, 1999 herein specifically incorporated by reference). It is well known in the art that Georgieff et al. (*J. Pediatr.,* 109: 316-321, 1986), herein specifically incorporated by reference, determined that using the mid arm/head circumference ratio is a better measurement of growth in infants than using the infant's birth weight. In this model, the best predictors of the mid arm/head circumference ratio, in descending order of variance, were: the mid thigh circumference, leptin, post-conceptional age, triceps skin fold, upper arm circumference, intake, calf circumference, crown rump length, and total body length (r=0.9, r-squared=0.81, p<0.00001). Of most importance, leptin itself accounted for 27% of the variance in mid arm/head circumference ratio. Leptin values in this group of premature infants were both affected by and predictive of neonatal growth. This expands the potential role of leptin as both an intrauterine and neonatal growth factor.

For the newborn infant (both full-term and premature), the physical benefits of breast-feeding are multiple and provide such diverse attributes as protection from infections (upper respiratory, intestinal and middle ear), and a decrease in atopic diseases. Many components of human breast milk have also been shown to be necessary for development of the brain, intestinal tract, spinal cord, and retina (Crawford M A et al., *A. J. Clin. Nutr.*, 31:2181-2185, 1978). In general, the bioavailability of human milk components is remarkably high and is superior compared to cow's milk or formula (Fuchs, A R: *Physiology and Endocrinology of Lactation*, p. 549-577. In Obstetrics: *Normal and Problem Pregnancies*, 1986).

Figure 2:
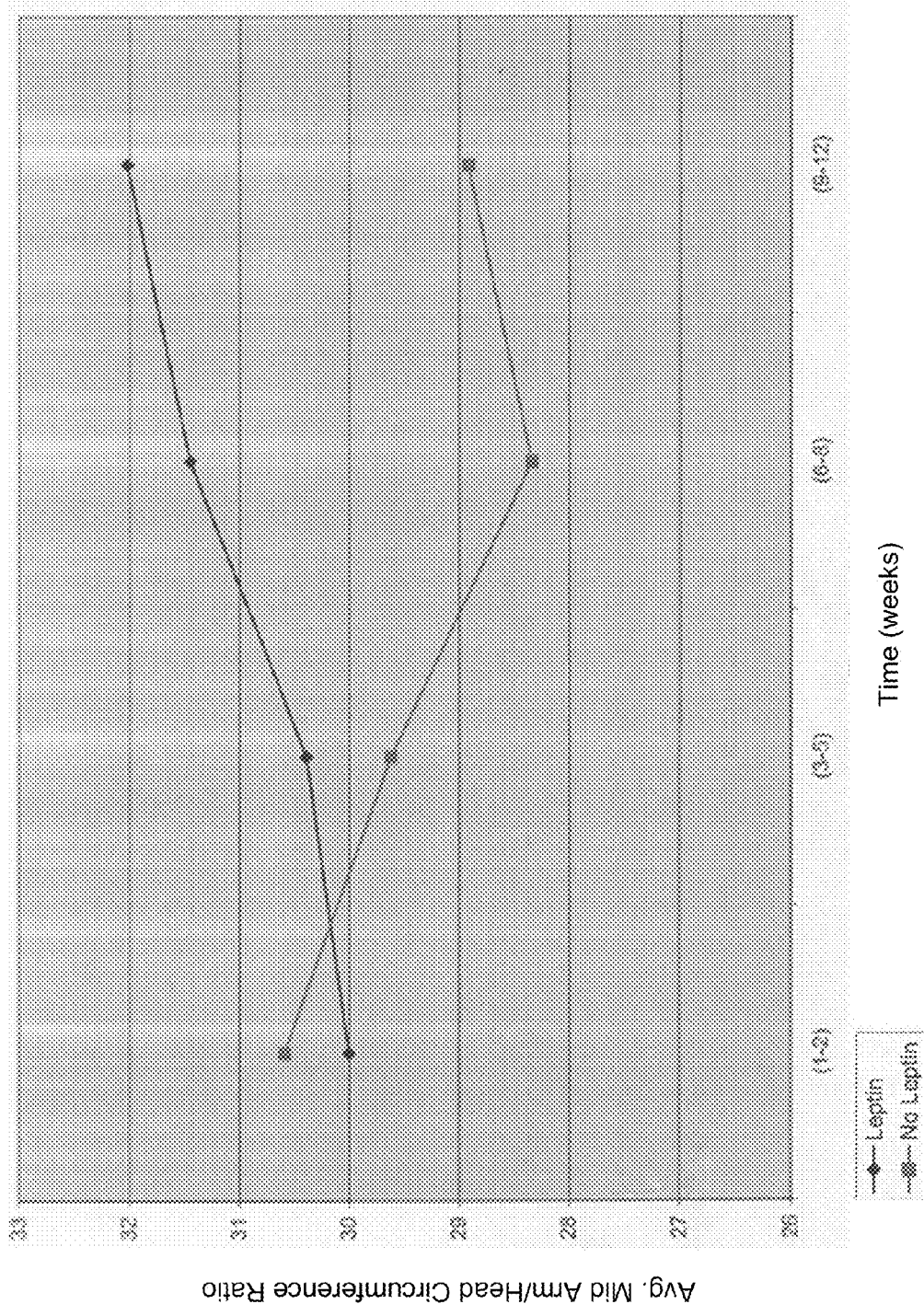
FIG. 2 is a plot of the average mid arm/head circumference ratio for breast-fed infants (leptin) and formula-fed infants (no leptin) as a function of time (weeks).

With reference now to FIG. 2, in a longitudinal study comparing various growth parameters in formula and breast-fed infants, breast-fed infants were found to grow at a faster rate than formula-fed infants. Leptin levels in breast milk increased during the 12 weeks of the study. In early and transitional milk, leptin levels were ~20 ng/ml; in mature milk, leptin levels were ~70 ng/ml, similar to that observed below in Example 1 regarding leptin levels in established breast milk (73.22±39.03 ng/ml, n=8). Together, the studies in premature and full-term infants indicate that leptin acts as a growth factor and not as a satiety factor in infants.

The present invention may be used to administer leptin to premature infants, low-birth weight infants, full-term infants with low leptin levels, and infants having a condition that may be treated with the administration of leptin. As used herein "infant" refers to normal infants, premature infants, low-birth weight infants, full-term infants with low leptin levels, and infants having a condition that may be treated with the administration of leptin. Prior to administering the isolated MFGs to an infant, the isolated MFGs should be resuspended in a liquid to produce suspended MFGs. The MFGs are preferably resuspended in a medium including, but not limited to, physiologic saline (0.9% wt/vol NaCl), water, intravenous solutions, human breast milk, milk, baby formula, or any other medium that is safe for infant administration. The isolated MFGs are preferrably resuspended at a concentration between about 50 ng/ml leptin to about 100 ng/ml leptin and most preferably resuspended at a concentration of 75 ng/ml.

The MFGs should be resuspended in a medium that is appropriate for the type of administration. If the MFGs are being administered orally or by other enteral means, resuspending the MFGs in a medium appropriate for infant consumption including, but not limited to, human breast milk, milk, baby formula, soy milk, water, or other liquid safe for human consumption is preferred. The isolated MFGs may be suspended in baby formula to provide a formula-feeding baby with a source of leptin. Further, the isolated MFGs may be added to human breast milk even if the infant is currently feeding from breast milk to supplement the breast milk with additional leptin.

If the MFGs are to be injected intravenously, subcutaneously, intraperitoneally, or intramuscularly, the MFGs should be suspended in an appropriate medium for injection to an infant. An appropriate medium includes, but is not limited to, physiologic saline, water, and intravenous solutions.

Additional supplements including nutrients, drugs, or other substances may be added to the suspended MFGs prior to administering the MFGs to the infant provided that the addition of the additional supplement does not prevent the effective administration of leptin to the infant. An effective amount of suspended MFGs is administered to the infant. MFGs are administered to infants at a dosage between about 0.5 ng leptin per gram body weight per feeding and about 1.0 ng leptin per gram body weight per feeding.

EXAMPLE 1

Determination of Leptin Levels in Breast Milk

Measurement of leptin in breast milk: All breast milk was obtained from donors who voluntarily consented to participate in the study. They were healthy women from the Research Department, between 25-35 yr of age, who planned to breast-feed and had delivered healthy full term infants. Milk was collected by either hand expression or a hand-held electric pump and stored frozen at −20° C. For leptin analysis, milk samples were thawed overnight in the refrigerator. Skim milk was prepared by centrifugation of whole milk at 13000 rpm for 10 min at 4° C. to separate milk fat from the liquid phase. A spatula was used to remove the layer of fat. Milk samples were sonicated for 3-10 sec bursts with 20 sec cooling intervals using a Branson Model W 180 sonicator with a stepped microtip. Radioimmunoassay (Lino Research, St. Charles, Mo.) for serum leptin was performed as described by the manufacturer.

Cytospin cell preparations: Human mammary epithelial cells were prepared for cytospin from at least 20 ml breast milk. Milk was spun at 2500 rpm, and the liquid and fat layers were removed. The pelleted cells were rinsed once in HBSS and then resuspended in HBSS. The cell suspension was transferred to disposable cytofunnels with attached cytospin slides and spun at 1000 rpm for 10 min in a Cytospin 3 (Shandon Inc., Pittsburgh, Pa.). Slides were stored frozen at −20° C.

Cell Culture: Human Mammary Epithelial Cells (HMEC) were obtained from Clonetics (San Diego, Calif.) and grown in serum-free MEGM medium (Clonetics). HMEC cells were mixed 1:1 with cold undiluted Matrigel (Collaborative Research, MA) by methods known to one skilled in the art, such as the method described in Gomm et al. (*J. Cell Physiol.*, 171:11-19) herein specifically incorporated by reference. Twenty-four well plates were seeded with this cellular mix and warmed to 37° C. for at least 30 min before being overlaid with the growth medium. Cells were allowed to grow for up to 3 weeks in culture during which time they continued to divide and fuse to form large aggregates of cells from which ducts were commonly seen.

Immunohistochemistry: Normal frozen breast tissue was obtained from Christiana Care, Inc. (Christiana, Del.), and 10 μm sections were cut and placed onto glass slides. These sections and the cytospin cell samples were fixed in Streck Tissue Fixative (Streck Laboratories Inc., Omaha, Nebr.) for 5 min at room temperature. HMEC cells grown in Matrigel were fixed overnight at 4° C. in the same fixative before the cellular gel was removed, mounted in 10% Tragacanth gum, snap-frozen in isopentane, and 10 μm sections prepared. Samples were then blocked with Peroxo-block and CAS block (Zymed, San Francisco, Calif.) according to the manufacturer's instructions. Superblock (Research Genetics; Huntsville, Ala.) was utilized to block background staining from Matrigel proteins. Polyclonal rabbit anti-leptin (RDI, Flanders, N.J.) was diluted 1:100 with serum blocking buffer and incubated for 60 min at room temperature. Antibody to epithelial membrane antigen (Zymed) was used neat; milk fat globule membrane antibody (Novocastra Laboratories, Ltd., Burlingame, Calif.) was diluted 1:50. A kit obtained from Zymed was used for subsequent steps for the biotinylated labeled secondary antibody and calorimetric detection with either DAB or AEC chromagen.

RT-PCR: Human mammary gland total RNA was obtained from Clontech (Palo Alto, Calif.), and adipose RNA was from Invitrogen (Carlsbad, Calif.). One microgram of total RNA was reverse-transcribed using avian myeloblastosis virus and oligo (dT) primer (Promega, Madison, Wis.), according to the manufacturer's instructions. Amplificaon of the cDNA sequence was performed by methods well known to one skilled in the art. For assessment of the relative levels of leptin to β-actin, a multiplex RT/PCR approach known to those skilled in the art was used, such as the method described by Dukas et al. (Anal. Biochem. 215:66-72, (1993) herein specifically incorporated by reference. Primer sequences for leptin and β-actin were those known in the art and descried previously in Hassink et al. (*Pediatrics*, 100:e1e6, 1997) herein specifically incorporated by reference. β-casein primers were:

```
                                      (SEQ ID NO.: 1)
CASF1: 5' ATTCTGCCTCTTGCTCAGCCTGC3';
and (SEQ ID NO.: 2)
CASR1: 5' AGCTCTCTGAGGGTAGGGCACCAC3'.
```

PCR products were separated on a 4% NuSieve (FMC Bioproducts, Rockland, Me.) agarose gel and stained with ethidium bromide.

Figure 3:
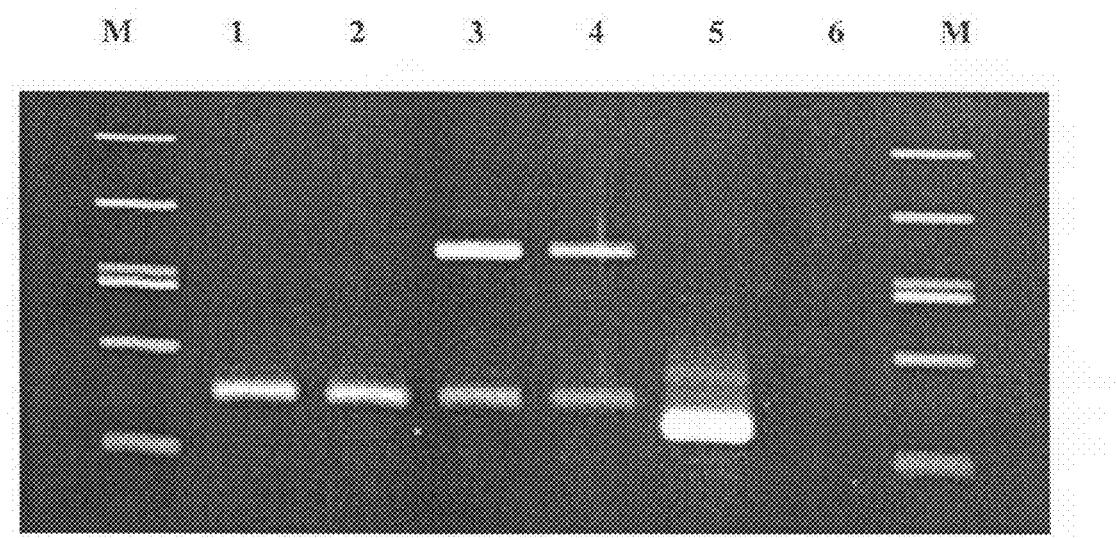
FIG. 3 is a RT/PCR analysis of leptin mRNA in mammary gland and adipose tissue. Total RNA was reversed transcribed from either mammary gland (lanes 1,3,5) or adipose (lanes 2,4,6) tissue and amplified with PCR primers to either leptin (lanes 1-2), both leptin and β-actin (lanes 3-4) or β-casein (lanes 5-6). Markers (M) are 1000, 700, 525, 500, 400, 300 bp. The size of the leptin RT/PCR product is 348 bp; β-actin is 592 bp; β-casein is 329 bp.

RT/PCR analysis of total RNA from mammary gland revealed the presence of leptin mRNA at a level comparable to that of adipose tissue (FIG. 3). Sequencing of the leptin cDNA product revealed complete sequence identity to that of placental and adipose leptin (GenBank accession number D9487). FIG. 3 also shows expression of β-casein, a marker of mammary epithelial cell differentiation, in the mammary gland, but not the adipose tissue RNA.

Figure 4:
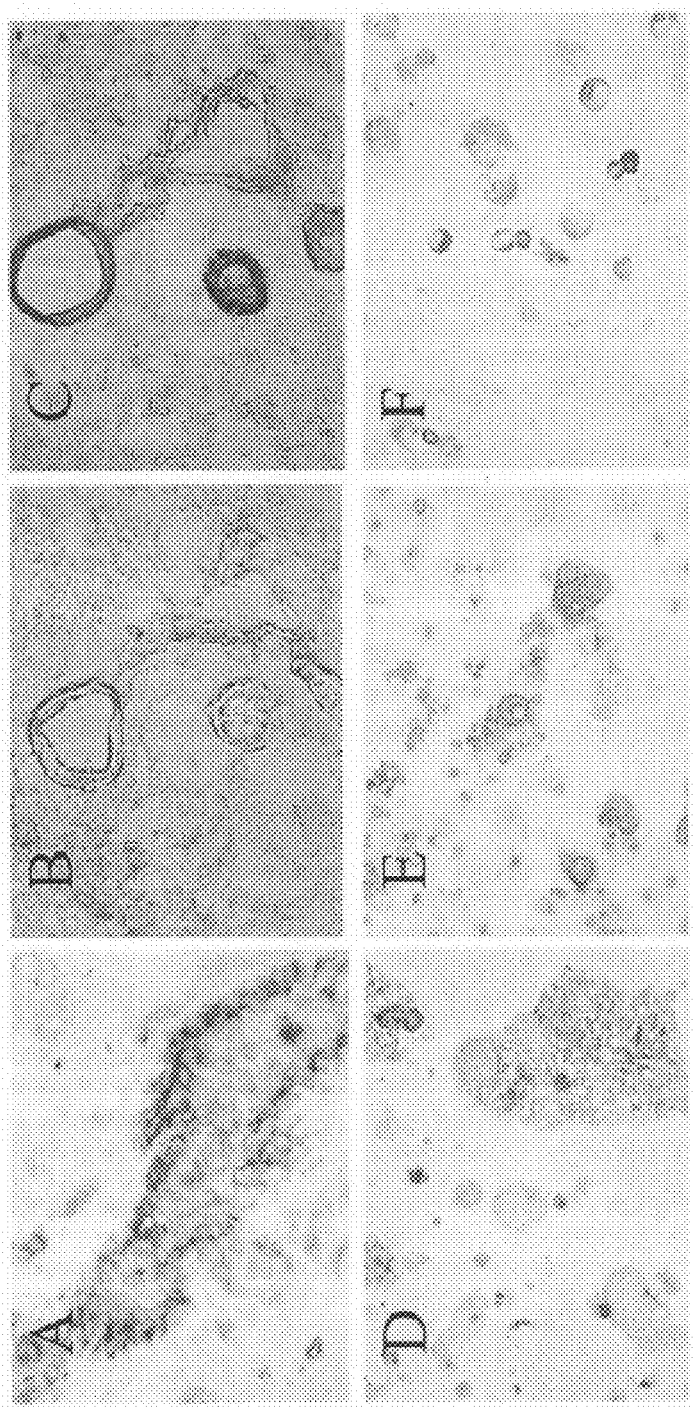
FIGS. 4A-4F show immunohistochemical detection of leptin in human breast tissue and mammary epithelial cells. Sections were stained for leptin or epithelial membrane antigen as described in the Methods. Colorimetric detection was with DAB (brownish purple stain) for panels A, D, and F or AEC (red stain) for panels B, C, and E. (A) Human breast tissue stained for letpin, counterstained with methyl green; (B) Cultured HMEC on Matrigel, no primary antibody; (C) Cultured HMEC on Matrigel stained with leptin; (D, E) Epithelial cells from cytospins of 6 mo post-partum breast milk stained with either (D) leptin, counterstained with methyl green or (E) epithelial membrane antigen, counterstained with Mayer's hematoxylin; (F) milk fat globules from cream of breast milk stained with leptin. (A-E), 245× magnification; (F), 612× magnification.

Immunohistochemical staining with a polyclonal antibody to human leptin showed leptin production by ductal epithelial cells of human breast tissue (FIG. 4A). FIG. 4C shows that cultured human mammary epithelial cells maintained on a Matrigel substrate also produce leptin. Finally, leptin was shown to be present in the secretory epithelial cells of breast milk (FIG. 4D). These cells, which are the predominant cell type shed into milk after the second month of lactation, were identified as epithelial cells by their positive staining for epithelial membrane antigen (FIG. 4E). Other abundant cell types in human milk include neutrophils and macrophages; these cell types did not express, leptin. Interestingly, intense immunostaining for leptin was observed in non-cellular vesicles of human milk (FIG. 4F). These vesicles also stained positively for milk fat globule protein (not shown). These results indicate that leptin is either present in, or associated with, the milk fat globules of breast milk.

Figure 5:
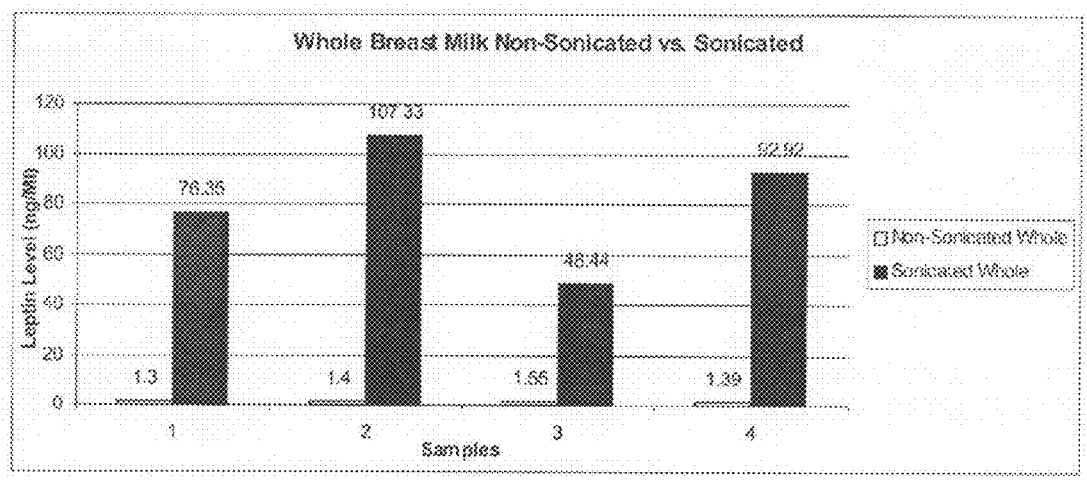
FIGS. 5A-5B are plots showing the effect of sonication on leptin levels in (A) whole and (B) skim milk. Milk samples were prepared and analyzed for leptin levels by radio immunoassay as described in the Methods. (■) sonicated; (□) not sonicated.
Figure 5:
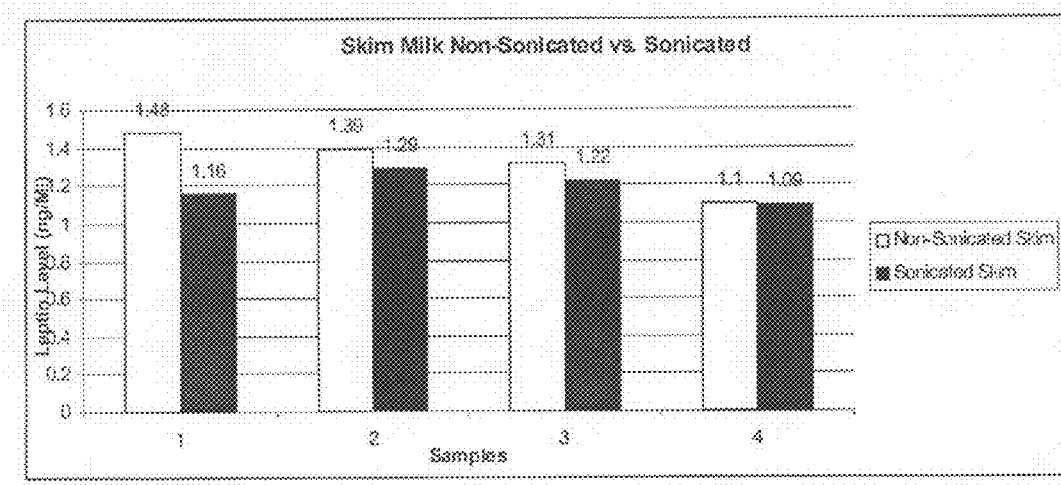

Immunoreactive leptin levels were higher in whole milk as compared to skim milk (FIG. 5A). However, it was critical to sonicate the milk sample to detect the high levels of leptin in whole milk. Sonication of skim milk samples made no difference in immunodetection of leptin (FIG. 5B). These data, together with the immunolocalization of leptin to milk fat globules described above, suggest that leptin is sequestered within these vesicles and not detectable by radioimmunoassay. Sonication disrupts the membrane vesicles and allows subsequent immunodetection of leptin.

This example shows that human mammary epithelial cells produce and secrete leptin. Furthermore, leptin is associated with milk fat globules, which partition into the lipid fraction of whole milk. These results explain why leptin is found in higher concentration in whole as compared to skim milk.

Without intending to be bound by theory, it is believed that milk fat globules are derived from the apical plasma membrane of the epithelial cell and the secretory vesicle membrane of the Golgi apparatus. The globules therefore consist of a lipid core enclosed by membrane and membrane-bound proteins that are produced in the Golgi. Leptin becomes part of the milk fat globule as it is processed in the Golgi apparatus. It is likely that the association of leptin with these globules confers a protective effect against degradation of leptin by the infant digestive tract.

Surprisingly, average leptin concentrations in breast milk (73.22±39.03 ng/ml, mean±SE, n=8) were higher than serum leptin levels in normal (7.5±9.3 ng/ml), obese (31.3±24.1 ng/ml), pregnant (29.8±17.0 ng/ml), or nursing (8.93±0.96 ng/ml) individuals. Although sonication was necessary to detect the high levels of leptin in whole breast milk, sonication of skim milk did not increase leptin levels. Thus, the mammary gland appears to produce high quantities of leptin, in agreement with the RT/PCR data (FIG. 3) showing similar levels of leptin mRNA in adipose and mammary gland tissues. Sequencing of the leptin cDNA product revealed complete sequence identity to that of placental and adipose leptin.

The low level of leptin that is detected in skim milk may arise from the maternal circulation and not the mammary gland. This would account for the high correlation between leptin levels in maternal serum and skim milk. It also would explain why sonication did not increase leptin levels in skim milk. However, the predominant source of leptin in breast milk appears to be the mammary gland. Putative roles of leptin in breast milk include a neonatal growth factor and a regulator of neonatal food intake.

EXAMPLE 2

Determination of Leptin Content in Lipase-Treated Milk Samples

In Example 1 it was critical to sonicate the milk sample to detect the high levels of leptin in whole milk. Occasionally, with high fat milk samples, sonication interfered with the leptin radioimmunoassay, and no pellet was formed in the assay. Without intending to be bound by theory, this is probably due to the formation of micelles in high fat sonicated milk samples. To attempt to circumvent this problem, we used pancreatic lipase to disrupt the MFG as described below.

Six hundred microliters of whole milk was incubated in a 37° C. water bath for 10 min. Six microliters of a 1 M sodium bicarbonate solution was then added in order to adjust the pH of the sample to approximately 8.0, the optimal pH for pancreatic lipase activity. Two and four-tenths microliters (30 U) of pancreatic lipase (Sigma Chemical Co., St. Louis, Mo.) was added to the milk sample, and the sample was incubated with constant shaking at 37° C. for 60 min. The sample was placed on ice and then assayed for leptin levels by radioimmunoassay as described above. The data in Table 1 show that it is possible to detect leptin levels in lipase-treated milk, even when the milk sample has a high fat content.

TABLE 1

Leptin levels (ng/ml) in sonicated and lipase-treated milk samples

| Whole | Whole-Sonicated | Whole-Lipase-treated |
|---|---|---|
| 0.68 | No pellet | 6.49 |

EXAMPLE 3

Isolation of Milk Fat Globules and Determination of Leptin Levels

MFGs were isolated by methods known to those skilled in the art such as the method described in Giuffrida et al. (*J. Prot Chem*, 17:143-148, 1998) herein specifically incorporated by reference. Fresh milk was collected from mothers enrolled in a Newborn growth study. Milk (10 ml) was transferred to a 15 ml centrifuge tube and spun at 2000 g for 20 minutes at room temperature. The supernatant (cream) was collected by pipetting and transferred to a 1.5 ml microfuge tube and centrifuged at 6° C. for 70 minutes at 100 g. MFGs were then collected by 'scooping' out the congealed cream with a sterile spatula, and transferred to a new 1.5 ml microfuge tube. MFGs were washed 3× with 0.9% (wt/vol) NaCl and centrifuged at 2000 g for 30 min at 6° C. Finally, MFGs were resuspended in a volume of saline commensurate with the starting volume of milk, in this case 10 ml. Leptin levels were measured by radioimmunoassay by using a kit commercially available from Linco, according to the manufacturer's instructions. Leptin levels in isolated intact MFGs were <0.5 ng/ml. Treatment of the MFGs with 50 U/ml pancreatic lipase for 60 min resulted in a final leptin concentration of 90.92 ng/ml.

To determine whether leptin could be fully recovered from milk that had been frozen and thawed, the same procedure was followed as described above. Leptin levels were compared in intact MFGs (untreated), sonicated MFGs, and MFGs treated with lipase. The data in Table 2 indicate that the recovery of leptin in MFGs from thawed milk is not as good as fresh milk. Thus, the preferred method of isolating MFGs is from fresh milk.

TABLE 2

Leptin levels (ng/ml) in MFGs purified from milk samples

| Sample No. | MFGs untreated | MFGs Sonicated | MFGs lipase-treated |
|---|---|---|---|
| 1 | <0.5 | <0.5 | 0.56 |
| 2 | <0.5 | <0.5 | 1.65 |
| 3 | 49.4 | 68.03 | 68.03 |
| 4 | <0.5 | <0.5 | 0.5 |
| 5 | <0.5 | 1.04 | <0.5 |
| 6 | <0.5 | <0.5 | 1 |
| 7 | <0.5 | <0.5 | 0.7 |
| 8 | <0.5 | <0.5 | 1.65 |

Those persons skilled in the art will therefore readily understand that the present invention is susceptible of a broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A composition, comprising:
   isolated and substantially purified milk fat globules containing leptin; and
   a medium that is effective for suspending the isolated and substantially purified milk fat globules and is safe to administer an effective amount of leptin to a subject.

2. The composition of claim 1, wherein the medium is selected from the group consisting of physiologic saline, water, breast milk, whole or skim milk, soy milk, intravenous solutions, and baby formula.

3. The composition of claim 1, wherein the isolated and substantially purified milk fat globules are suspended in the medium at a concentration in the range of about 50 ng/ml leptin to about 100 ng/ml leptin.

4. The composition of claim 1, wherein the isolated and substantially purified milk fat globules are suspended in said medium at a concentration of about 75 ng/ml.

5. The composition of claim 1, wherein the composition is suitable for oral administration.

6. The composition of claim 1, wherein the composition is suitable for an administration route selected from the group consisting of intravenously, subcutaneously, intraperitonally, and intramuscularly.

7. The composition of claim 1, wherein the composition further comprises an additive.

8. The composition of claim 7, wherein the additive is one or more compounds selected from the group consisting of vitamins, supplements, nutrients, and drugs.

9. The composition of claim 1, wherein the milk fat globules contain a native form of leptin.

10. The composition of claim 1, wherein the isolated and substantially purified milk fat globules are obtained from a milk-producing mammal that produces milk fat globules containing a native form of leptin.

11. The composition of claim 10, wherein the mammal is selected from the group consisting of humans, cows, rats, mice and goats.

12. The composition of claim 1, wherein at least a portion of the leptin is contained within the milk fat globule.

13. The composition of claim 1, wherein the subject is a human.

14. The composition of claim 1, wherein the subject is an infant.

15. The composition of claim 14, wherein the infant is a small-for-gestational-age infant.

16. The composition of claim 14, wherein the infant is a premature infant.

17. The composition of claim 14, wherein the infant has low leptin levels.

18. The composition of claim 14, wherein the infant is a small-for-gestational-age infant.

19. The composition of claim 14, wherein the infant is a low-birth-weight infant.

20. The composition of claim 14, wherein the infant is a formula-fed infant.

21. The composition of claim 1, wherein the effective amount of leptin is in the range of about 0.5 ng to about 1.0 ng leptin per gram of infant body weight per feeding.

22. The composition of claim 1, wherein the subject has a condition selected from the group consisting of obesity, sterility, sexual immaturity, malnutrition, compromised immunity, psychiatric disorders, and diabetes.

23. The composition of claim 1, wherein the milk fat globules are isolated and substantially purified from fresh milk.

* * * * *